(12) United States Patent
Aszodi et al.

(10) Patent No.: US 6,875,752 B2
(45) Date of Patent: Apr. 5, 2005

(54) URIDINE DERIVATIVES AS ANTIBIOTICS

(75) Inventors: Jozsef Aszodi, Tucson, AZ (US); Christophe Dini, Le Plessis Pate (FR); Jean-Claude Guillot, Noisy le Sec (FR); Stanislas Didierlaurent, Lagny sur Marne (FR); Nathalie Drochon, Vitry sur Seine (FR); Jidong Zhang, Paris (FR)

(73) Assignee: Aventis Pharma S.A. (FR)

( * ) Notice: Subject to any disclaimer, the term of this patent is extended or adjusted under 35 U.S.C. 154(b) by 202 days.

(21) Appl. No.: 10/258,759
(22) PCT Filed: May 4, 2001
(86) PCT No.: PCT/FR01/01356

§ 371 (c)(1),
(2), (4) Date: Oct. 25, 2002

(87) PCT Pub. No.: WO01/85750

PCT Pub. Date: Nov. 15, 2001

(65) Prior Publication Data

US 2003/0130227 A1 Jul. 10, 2003

(51) Int. Cl.$^7$ .................. A01N 43/04; A61K 31/70; C07H 19/06
(52) U.S. Cl. ............... 514/50; 514/49; 536/28.4; 536/28.53
(58) Field of Search ............... 536/28.4, 28.53; 514/49, 50

(56) References Cited

FOREIGN PATENT DOCUMENTS

| JP | 02306992 | | 12/1990 |
| JP | 02 306992 A | * | 12/1990 |
| JP | 05078385 | | 3/1993 |
| JP | 05 078385 A | * | 3/1993 |
| WO | 9741248 | | 11/1997 |

OTHER PUBLICATIONS

Hampton et al., "Design of Species– or Isozyme–Specific Enzyme Inhibitors, Part 1 . . . ", Journal of Medicinal Chemistry, 1979, vo 22, No. 6, pp. 621–631.*

Hampton et al., "Design of Species– or Isozyme–Specific Enzyme Inhibitors, Part 2 . . . ", Journal of Medicinal Chemistry, 1979, v 22, No. 12, pp. 1524–1528.*

M. Ubukata et al, "The . . . Synthesis", J. Am. Chem. Soc. vol. 110, No. 13, 1988, pp. 4416–4417.

Imura et al, "Liposidomycin . . . coli Y–10", Agric. Biol. Chem., vol. 53, No. 7, 1989, pp. 1811–1815.

Knapp et al, "Synthesis . . . Diazepanone", Tetrahedron Letters, vol. 33, No. 35, 1999, pp. 5435–5486.

M. Ubukata, "Chemical . . . Antibiotics", Journal of Japan Society for Bioscience, Biotechnology and Agrochemistry, vol. 62, No. 11, 1988, pp. 1629–1636, no translation provided.

M. Ubukata et al, "structure . . . Antibiotics", J. Org. Chem., vol. 57 No. 24, 1992 pp. 6392–6403.

* cited by examiner

Primary Examiner—James O. Wilson
Assistant Examiner—Traviss C. McIntosh, III
(74) Attorney, Agent, or Firm—Muserlian, Lucas and Mercanti

(57) ABSTRACT

All possible isomeric forms of a compound of the formula where the substituents are defined as in the specification and its non-toxic, pharmaceutically acceptable salts useful as antibiotics.

16 Claims, No Drawings

URIDINE DERIVATIVES AS ANTIBIOTICS

This application is a 371 of PCT/FR01/01356 filed May 4, 2001.

The present invention relates to new derivatives of uridine, their preparation process and their use as medicaments.

A subject of the invention is, in all possible isomer forms as well as their mixtures, the compounds of formula (I):

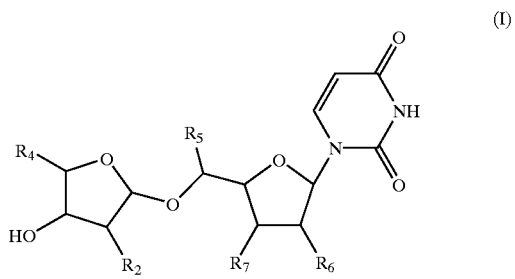

in which $R_2$ represents a hydrogen or halogen atom, an alkyl, alkenyl or alkynyl radical containing up to 12 carbon atoms, an OH, O-alkyl, OCO-alkyl radical containing up to 18 carbon atoms, an O-aryl or OCO-aryl radical containing up to 15 carbon atoms, $R_4$ represents a $CH_2NH_2$, $CH_2NH$alkyl radical containing up to 18 carbon atoms, $CH_2N$ (alkyl1) (alkyl2) in which alkyl1 and alkyl2 identical to or different from one another represent a linear or branched alkyl radical containing up to 18 carbon atoms, or $R_4$ represents an optionally substituted $CH_2$-guanidine or optionally substituted $CH_2$-amidine radical, a $CH_2$-heterocycle, $CH_2$—NH-heterocycle or $CH_2$—NH-aryl or $CH_2$—NH-heteroaryl radical optionally substituted, $R_5$ represents a

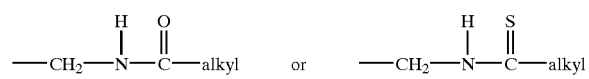

radical containing up to 24 carbon atoms, a

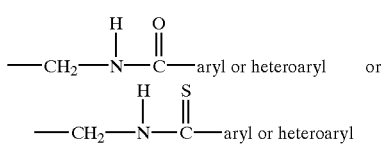

radical containing up to 24 carbon atoms, a $CH_2N_3$ radical, a:

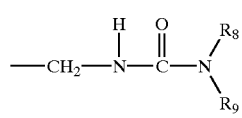

radical a:

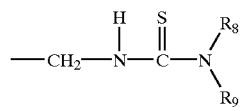

radical a:

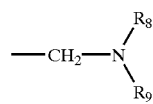

radical
with $R_8$ representing a hydrogen atom or an alkyl radical containing up to 4 carbon atoms,
and $R_9$ representing an alkyl radical, linear or branched containing at most 18 carbon atoms, a carbocyclic or heterocyclic radical containing 5 or 6 members, an aryl or heteroaryl radical optionally substituted, $R_8$ and $R_9$ also being able to form with the nitrogen atom which carries them an optionally substituted heterocycle, or $R_5$ represents a $CH_2$alkyl, $CH_2$-aryl or $CH_2$-heteroaryl radical optionally substituted, $CH_2$Oalkyl or $CO_2$alkyl radical containing up to 18 carbon atoms, or $CH_2$S-alkyl radical containing up to 16 carbon atoms, or $CH_2$S-aryl or $CH_2$S-heteroaryl radical optionally substituted, $R_6$ represents a hydrogen or halogen atom, an OH, O-alkyl or OCO-alkyl radical containing up to 18 carbon atoms, an S-alkyl, S-aryl or S-heteroaryl radical containing up to 12 carbon atoms, all the alkyl, aryl, heteroaryl radicals, the carbocyclic and heterocyclic radicals defined above being optionally substituted by one or more radicals chosen from the halogen atoms; the hydroxyl radical; the linear or branched alkyl or alkoxy radicals containing 1 to 4 carbon atoms; the phenyl and phenylalkyl radical, the phenyl radical itself being optionally substituted by a halogen atom or a phenyl radical and the linear or branched alkyl radical containing 1 to 4 carbon atoms; a carbocyclic radical containing 4 or 6 members;

$R_7$ represents a hydrogen atom or a free, etherified or esterified OH radical,
as well as the addition salts with acids of the compounds of formula (I).

Among the addition salts with acids, there can be mentioned those formed with mineral acids, such as hydrochloric, hydrobromic, sulphuric or phosphoric acid or with organic acids such as formic, acetic, trifluoroacetic, propionic, benzoic, maleic, fumaric, succinic, tartaric, citric, oxalic, glyoxylic, aspartic acids, alkanesulphonic acids, such as methane or ethane sulphonic acid, arylsulphonic acids such as benzene or paratoluene sulphonic acids.

In the definition of substituents:
the halogen is preferably fluorine, bromine or chlorine,
The linear or branched alkyl radicals can contain up to 24 carbon atoms, the linear or branched alkenyl and alkynyl radicals can contain up to 12 carbon atoms. These alkyl, alkenyl and alkynyl radicals are chosen from radicals well known to a person skilled in the art.

the alkyl, alkenyl or alkynyl radical can represent for example a methyl, ethyl, n-propyl, isopropyl, n-butyl isobutyl, terbutyl, decyl or dodecyl, vinyl, allyl, ethynyl, propynyl, cyclobutyl, cyclopentyl or cyclohexyl radical, the aryl radical is preferably the phenyl or naphthyl radical, the heterocyclic radical can preferably represent the pyrrolyl, pyrrolidinyl, pyridyl, pyrazinyl, pyrimidyl, piperidinyl, piperazinyl, quinuclidinyl, oxazolyl, isoxazolyl, morpholinyl, indolyl, imidazolyl, benzimidazolyl, triazolyl, thiazolyl, azetidinyl or aziridinyl radical.

The carbocyclic radical can represent in particular a cyclopentyl or cyclohexyl radical.

A more particular subject of the invention is the previously defined compound of formula (IA):

(IA)

in which the various substituents retain the same meaning as previously.

Among the preferred compounds of the invention, there can be mentioned:

the compounds of formula (I) in which $R_7$ represents a hydrogen atom, the compounds of formula (I) in which $R_6$ represents an OH radical or a fluorine atom, the compounds of formula (I) in which $R_2$ represents an OH radical, the compounds of formula (I) in which $R_2$ represents a fluorine atom, the compounds of formula (I) in which $R_4$ represents a $CH_2NH_2$ radical, the compounds of formula (I) in which $R_4$ represents a $CH_2NHCH_3$ or $CH_2NHC_2H_5$ radical, the compounds of formula (I) in which $R_5$ represents a $$-CH_2-NH-\underset{\underset{O}{\|}}{C}-C_{15}H_{31}$$

radical the compounds of formula (I) in which $R_5$ represents a $$-CH_2-\underset{\underset{CH_3}{|}}{N}-(CH_2)_{11}CH_3, \quad -CH_2-\underset{\underset{H}{|}}{N}-(CH_2)_6CH_3$$

$$-CH_2-\underset{\underset{H}{|}}{N}-(CH_2)_{11}CH_3 \quad \text{or}$$

$$-CH_2-\underset{\underset{H}{|}}{N}-\text{[biphenyl-cyclohexyl]}$$

or $CH_2$—NH-alkyl radical with linear or branched alkyl containing 8 to 14 carbon atoms.

Among the compounds of the invention, there can be mentioned the compounds the preparation of which is given hereafter in the experimental part and quite particularly the product of Example 1 and its salts. There can be mentioned for example the trifluoroacetate of Example 1.

The compounds of the invention have useful antibiotic properties. They have a very good antibiotic activity in particular on gram$^+$ bacteria such as staphylococci, streptococci, pneumococci and enterococci.

The compounds of the invention can therefore be used as medicaments in the treatment of germ-sensitive infections and in particular in that of staphylococcia, such as malignant facial or cutaneous staphylococcia, pyodermatitis, septic or suppurating wounds, boils, anthrax, phlegmons, erysipelas and acne, staphylococcia such as acute primitive or post-influenzal angina, bronchopneumonia, pulmonary suppuration, streptococcia such as acute angina, otitis, sinusitis, scarlet fever, pneumococcia such as pneumonia, bronchitis, brucellosis, diphtheria, gonococcemia.

The products of the present invention can also be used against infections caused by germs such as Haemophilus influenzae, Rickettsia, Mycoplasma pneumoniae, Chlamydia, Legionella, Ureaplasma, Toxoplasma, or germs of the Mycobacterium genus.

A subject of the present invention is also therefore as medicaments and in particular as antibiotic medicaments, the products of formula (I) as defined above, as well as their addition salts with pharmaceutically acceptable mineral or organic acids.

A more particular subject of the invention is, as a medicament and in particular an antibiotic medicament, the product of Example 1 and its pharmaceutically acceptable salts.

A subject of the invention is also pharmaceutical compositions containing as active ingredient at least one of the medicaments defined above.

These compositions can be administered by buccal, rectal, parenteral route or by local route as a topical application on the skin and the mucous membranes, but the preferred route of administration is the buccal or parenteral route.

They can be solids or liquids and be presented in the pharmaceutical forms commonly used in human medicine, such as for example, plain or sugar coated tablets, gelatin capsules, granules, suppositories, injectable preparations, ointments, creams, gels; they are prepared according to the usual methods. The active ingredient or ingredients can be incorporated with excipients usually used in these pharmaceutical compositions, such as talc, gum arabic, lactose, starch, magnesium stearate, cocoa butter, aqueous or non aqueous vehicles, fatty substances of animal or vegetable origin, paraffin derivatives, glycols, various wetting, dispersing or emulsifying agents, preservatives.

These compositions can also be presented in the form of a powder intended to be dissolved extemporaneously in an appropriate vehicle, for example sterile apyrogenic water.

The dose administered is variable according to the condition treated, the patient in question, the administration route and the product considered. It can be, for example, comprised between 50 mg and 300 mg per day by oral route in adults for the product of Example 1 in one or more doses.

A subject of the invention is also a process for the preparation of the compounds of formula (I) characterized in that a compound of formula (II):

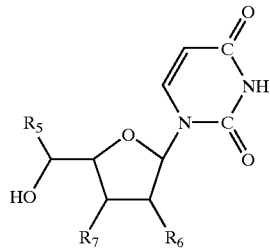

in which the various substituents retain their previous meaning is subjected to the action of a compound of formula (III):

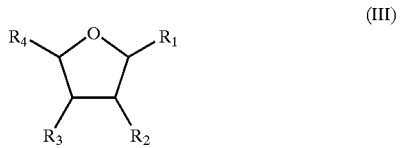

in which $R_1$ represents a halogen atom or an OC(NH)C(Hal)$_3$ radical with Hal representing a halogen atom or a

radical with R representing an alkyl radical containing up to 18 carbon atoms the other substituents $R_2$, $R_3$ and $R_4$ retaining their previous meaning in order to obtain the corresponding compound of formula (I) which is subjected if desired to one or more of the following operations: addition, substitution, condensation and salification in order to obtain the sought compound of formula (I).

The compounds of formula (II) used as starting products are new products which can be prepared as indicated hereafter in the experimental part.

The following examples illustrate the invention without however limiting it.

EXAMPLE 1

1-[5-O-(5-amino-5-deoxy-.beta.-D-ribofuranosyl)-3,6-dideoxy-6-[(1-oxohexadecyl)amino]-.beta.-D-ribo-hexofuranosyl]-2,4-(1H,3H)-pyrimidinedione STAGE A: 1-[2-O-acetyl-3,6-dideoxy-5-O-[(4-methoxyphenyl)methyl]-6-[(1-oxohexadecyl)amino]-.beta.-D-ribo-hexofuranosyl]-2,4-(1H,3H)-pyrimidinedione A mixture containing 450 mg of the product of Stage E, prepared as indicated below (Preparation 1), 25 ml of ethyl acetate, 590 mg of palmitic anhydride and 120 mg of palladium on carbon are agitated under a hydrogen atmosphere for 16 hours followed by filtering, evaporating and drying. 940 mg of product is obtained which is used as it is in the following stage.

STAGE B: 1-[2-O-acetyl-3,6-dideoxy-6-[(1-oxohexadecyl)amino]-.beta.-D-ribo-hexofuranosyl]-2,4-(1H,3H)-pyrimidinedione 240 mg of the product of Stage A dissolved in 2 ml of methylene chloride is added to 7.5 ml of a mixture of methylene chloride/trifluoroacetic acid (9/1) under a nitrogen atmosphere. The solution obtained is agitated for 1 hour followed by evaporating and drying. A product is obtained which is taken up in ether then in pentane followed by evaporation again. The product obtained is chromatographed and 47 mg of sought product is obtained.

STAGE C: 1-[2-O-acetyl-5-O-(5-azido-2,3-di-O-acetyl-5-deoxy-.beta.-D-ribofuranosyl)-3,6-dideoxy-6-[(1-oxohexadecyl)amino]-.beta.-D-ribo-hexofuranosyl]-2,4-(1H,3H)-pyrimidinedione 330 μl of SnCl$_4$ (1M solution in CH$_2$Cl$_2$) is added at 0° C. to a mixture of 120 mg of the product of the preceding stage, 132 mg of 5-azido-5-deoxy-.beta.-D-ribofuranose 1,2,3-triacetate and 1 ml of methylene chloride followed by agitating overnight at ambient temperature. 3 ml of methylene chloride and 2 ml of sodium acid carbonate are added followed by agitating for 15 minutes at ambient temperature, filtering, separating the organic phase and drying. After evaporation and chromatography on silica, 64 mg of sought product is recovered which is used as it is in the following stage.

STAGE D: 1-[5-O-(5-azido-5-deoxy-.beta.-D-ribofuranosyl)-3,6-dideoxy-6-[(1-oxohexadecyl)amino]-.beta.-D-ribo-hexofuranosyl]-2,4-(1H,3H)-pyrimidinedione A mixture of 64 mg of the product of the preceding stage and 2 ml of a 0.1 M solution of sodium methylate in methanol is kept under agitation for 15 hours. 2 ml of methanol and IR 120H$^+$ resin are added followed by filtering, evaporating, and 52 mg of sought product is obtained.

STAGE E: 1-[5-O-(5-amino-5-deoxy-.beta.-D-ribofuranosyl)-3,6-dideoxy-6-[(1-oxohexadecyl)amino]-.beta.-D-ribo-hexofuranosyl]-2,4-(1H,3H)-pyrimidinedione A mixture of 20 mg of the product of the preceding stage, 1 ml of methanol, 26.5 mg of palladium on carbon at 15% is agitated under a hydrogen atmosphere for 3 hours 30 minutes followed by filtering, rinsing and concentrating. 16 mg of sought product is obtained.

EXAMPLE 2

1-[6-azido-5-O-[2,5-dideoxy-5-(ethylamino)-2-fluoro-.beta.-D-arabinofuranosyl]-2-fluoro-2,3,6-trideoxy-.beta.-D-ribo-hexofuranosyl]-2,4-(1H,3H)-pyrimidinedione (4-methylphenyl)sulphonate STAGE A: 2-deoxy-2-fluoro-D-arabinose 3,5-dibenzoate 100 ml of a 5% solution of sodium acid carbonate at 5% in water is added to a mixture of 9.05 g of 3,5-dibenzoate of 2-deoxy-2-fluoro-alpha-D-arabinose bromide and 90 ml of acetone. 50 ml of water is added followed by agitating for 3 hours 30 minutes, diluting, extracting with methylene chloride, drying, filtering and evaporating to dryness.

STAGE B: 2-deoxy-2-fluoro-D-arabinose 3,5-dibenzoate and 1-(2,2,2-trichloroethanimidate)

A mixture of 7.4 g of the product of Stage A, 670 mg of cesium carbonate and 4.12 ml of trichloroacetonitrile is kept under agitation for 2 hours followed by filtering by rinsing with methylene chloride, and the solvent is evaporated off. 9.45 g of sought product is obtained.

STAGE C: 1-[6-azido-5-O-(2-deoxy-3,5-di-O-benzoyl-2-fluoro-.beta.-D-arabinofuranosyl)-2-fluoro-2.3,6-trideoxy-.beta.-D-ribo-hexofuranosyl]-2,4-(1H,3H)-pyrimidinedione A mixture of 715 mg of the product of the preceding stage and 270 mg of 1-(6-azido-2-fluoro-2,3,6-trideoxy-beta-D-ribo-hexofuranosyl)-2,4-(1H,3H)-pyrimidinedione (Preparation 2) and 10 ml of methylene chloride is cooled down to −30° C. 205 μl of TMSOTf (trimethylsilyl trifluoromethanesulphonate) is added followed by agitating for 6 hours. A solution of sodium acid carbonate is added at 0° C. followed by extracting, and the organic phase is recovered on methylene chloride followed by drying, filtering and evaporating the solvent. A product is obtained which is chromatographed on silica eluting with a methylene chloride/ethyl acetate (8/2) mixture. 152 mg of sought product is obtained.

STAGE D: 1-[6-azido-5-O-(2-deoxy-2-fluoro-.beta.-D-arabinofuranosyl)-2-fluoro-2,3,6-trideoxy-.beta.-D-ribo-hexofuranosyl]-2,4-(1H,3H)-pyrimidinedione 152 mg of the product of the preceding stage is taken up in 2 ml of a 0.1 M solution of MeONa/MeOH under magnetic stirring at ambient temperature. IR 120 H$^+$ is added until a neutral pH is reached followed by filtering by rinsing with methanol and evaporating the methanol, purifying by filtering on a silica cartridge eluting with methylene chloride, then with a methylene chloride/methanol mixture (9/1). 98 mg of sought product is obtained.

STAGE E: 1-[6-azido-5-O-[2-deoxy-2-fluoro-5-O-[(4-methylphenyl)sulphonyl]-.beta.-D-arabinofuranosyl]-2-fluoro-2,3,6-trideoxy-.beta.-D-ribo-hexofuranosyl]-2,4-(1H,3H)-pyrimidinedione 403 mg of the product of the preceding stage is solubilized in 2 ml of pyridine under an argon atmosphere and magnetic stirring. 225 mg of tosyl chloride is added followed by washing with a 10% solution of sodium hydrogen sulphate, then with sodium acid carbonate then with a saturated aqueous solution of NaHCO$_3$, then with water. After filtering and drying over sodium sulphate, the residue is chromatographed on silica eluting with a methylene chloride/methanol mixture (97/3). 360 mg of sought product is obtained.

STAGE F: 1-[6-azido-5-O-[2,5-dideoxy-5-(ethylamino)-2-fluoro-.beta.-D-arabinofuranosyl]-2-fluoro-2,3,6-trideoxy-.beta.-D-ribo-hexofuranosyl]-2,4-(1H,3H)-pyrimidinedione (4-methylphenyl)sulphonate A mixture of 80 mg of the previous product, 2 ml of a 33% aqueous solution of ethylamine is maintained at 60° C. for 18 hours. The product obtained is chromatographed on silica eluting with a methylene chloride/methanol mixture (8/2). 37 mg of sought product is obtained.

Preparation 1

1-[6-azido-3,6-dideoxy-5-O-[(4-methoxyphenyl) ethyl]-.beta.-D-ribo-hexofuranosyl]-2,4-(1H,3H)-pyrimidineione STAGE A: 6-azido-3,6-dideoxy-1,2-O-(1-methylethylidene)-.alpha.-D-ribo-hexofuranose 200 mg of 5,6-anhydro-3-deoxy-1,2-O-(1-methylethylidene)-.alpha.-D-ribo-hexofuranose dissolved in 2 ml of DMF is heated at 60° C. for 15 minutes. 350 μl of methanol and 300 μl of TMSN$_3$ are added followed by agitating at 60° C. for 48 hours, cooling down, diluting with methylene chloride, washing and drying. A product is obtained which is taken up in methanol. IRA 120H$^+$ resin is added followed by agitating for 10 minutes at ambient temperature, filtering, rinsing and concentrating to dryness. 230 mg of sought product is obtained.

STAGE B: 6-azido-3,6-dideoxy-5-O-[(4-methoxyphenyl) methyl]-1,2-O-(1-methylethylidene)-.alpha.-D-ribo-hexofuranose 6.27 g of sodium hydride is added at 0° C. to a solution containing 20 g of product prepared in the preceding stage and dissolved in DMF. 14.15 ml of PMBC1 (paramethoxybenzyl chloride) is added and the reaction medium is agitated for 1 hour at ambient temperature followed by cooling down to 0° C., and 3 ml of methanol is added. Agitation is carried out for 30 minutes at ambient temperature followed by filtering, adding chloroform and concentrating to dryness. 31.7 g of sought product is obtained.

STAGE C: 6-azido-3,6-dideoxy-5-O-[(4-methoxyphenyl) methyl]-.alpha.-D-ribo-hexofuranose A solution containing 34.8 g of the product of Stage B and 500 ml of a 50% aqueous solution of acetic acid is agitated at 40° C. for 24 hours followed by agitating for 36 hours at 40° C., diluting with a liter of water, extracting with ethyl acetate, drying, filtering and evaporating. Chromatography is carried out on silica eluting with a methylene chloride/ethyl acetate mixture (99.5/0.5) and 12.5 g of expected product is recovered.

STAGE D: 6-azido-3,6-dideoxy-5-O-[(4-methoxyphenyl) methyl]-D-ribo-hexofuranose 1,2-diacetate A solution of 10 g of the product of the preceding stage in 200 ml of pyridine is agitated under an argon atmosphere. 130 ml of acetic anhydride is added followed by agitating for 2 hours, cooling down to 0° C. for 15 minutes and adding 200 ml of methanol. After the solvent is evaporated off, a product is obtained which is taken up in methylene chloride, washed with 0.1 M hydrochloric acid and with an aqueous solution of sodium chloride. After filtering, drying and evaporating the methylene chloride, 12.43 g of sought product is obtained.

STAGE E: 1-[2-O-acetyl-6-azido-3,6-dideoxy-5-O-[(4-methoxyphenyl)methyl]-.beta.-D-ribo-hexofuranosyl]-2,4-(1H,3H)-pyrimidinedione A mixture of 3.58 g of uracile, 120 ml of acetonitrile, 8 ml of BSA N—O, bis-trimethylsilylacetamide and 11.43 g of the product of the previous stage in solution in 275 ml of acetonitrile is maintained under agitation and an argon atmosphere for one hour. 9.58 ml of trimethylsilyl bromide is added. The reaction medium is kept under agitation for 18 hours, 20 ml of triethylamine is added. The acetonitrile is evaporated off followed by taking up in methylene chloride, washing with a 1 M aqueous solution of methylene chloride, then with an aqueous solution of sodium chloride, drying and concentrating to dryness. After filtering on silica eluting with a methylene chloride/methanol mixture (98/2), 9.98 g of sought product is obtained.

Preparation 2

1-(6-azido-2-fluoro-2,3,6-trideoxy-.beta.-D-ribo-hexofuranosyl)-2,4-(1H,3H)-pyrimidinedione STAGE A: 1-[6-azido-3,6-dideoxy-5-O-[(4-methoxyphenyl)ethyl]-.beta.-D-ribo-hexofuranosyl]-2,4-(1H,3H)-pyrimidineione 10 g of the product of preparation 1 is dissolved in 300 ml of a 0.1 M solution of sodium methylate in methanol. After agitating for 15 minutes, the reaction medium is adjusted to pH 6, filtered, rinsed with methanol and the methanol is evaporated off. 8.7 g of sought product is obtained.

STAGE B: 1-[6-azido-3,6-dideoxy-5-O-[(4-methoxyphenyl)methyl]-2-O-(methylsulphonyl)-.beta.-D-ribo-hexofuranosyl]-2,4-(1H,3H)-pyrimidinedione 8.7 g of the product prepared in the preceding stage is dissolved in 200 ml of acetone. 5.9 ml of triethylamine and 2.5 ml of mesyl chloride are added at 0° C. After agitating for 1 hour at 0° C., 5.9 ml of triethylamine and 2.5 ml of mesyl chloride are added and the reaction medium is left under agitation for 2 more hours. The acetone is evaporated off, followed by taking up in ethyl acetate, washing with a 1 M solution of hydrochloric acid then with an aqueous solution of sodium chloride, drying, and the ethyl acetate is evaporated off. 10.63 g of sought product is obtained.

STAGE C: [2R-(2.alpha.,3a.beta.,9a.beta.)]-2-[2-azido-1(S)-[(4-methoxyphenyl)methoxy]ethyl]-6H-furo[2',3':4.5]oxazolo [3,2-a]pyrimidin-6-one 10.63 g of the product of the previous stage is dissolved in 400 ml of acetinitrile. 5 ml of DBU is added. After 30 minutes, the acetonitrile is evaporated off, followed by washing with a 0.1 M aqueous solution of hydrochloric acid, then with potassium acid carbonate, then with water, filtering, and the solvent is evaporated off. 9.53 g of sought product is obtained.

STAGE D: 1-[6-azido-3,6-dideoxy-5-O-[(4-methoxyphenyl)methyl]-.beta.-D-lyxo-hexofuranosyl]-2,4-(1H,3H)-pyrimidinedione 150 ml of a 1 M solution of soda is added to a solution of 9.53 g of the product of the preceding stage in 400 ml of acetonitrile. 150 ml of 1 M soda is added followed by agitating overnight. A solution of 1 M hydrochloric acid is added until a pH equal to 7 is obtained. The acetonitrile is evaporated off followed by taking up in ethyl acetate, washing, drying, filtering and evaporating in ethyl acetate. 9.03 g of sought product is obtained.

STAGE E: 1-[6-azido-2-fluoro-5-O-[(4-methoxyphenyl)methyl]-2,3,6-trideoxy-.beta.-D-ribo-hexofuranosyl]-2,4-(1H,3H)-pyrimidinedione 1 g of the product of the previous stage is dissolved in 20 ml of methylene chloride. 10 ml of pyridine is added followed by cooling down to 0° C., and 6 ml of DAST is added. After agitating for 4 hours, the reaction mixture is poured into a mixture of ice and sodium acid carbonate followed by agitating, filtering, rinsing with methylene chloride, washing, extracting, drying, filtering and evaporating the solvent. A product is obtained which is taken up in toluene and evaporated to drive off the pyridine. After chromatography on silica eluting with a methylene chloride/ethyl acetate mixture (8/2), 1 g of sought product is obtained.

STAGE F: 1-(6-azido-2-fluoro-2,3,6-trideoxy-.beta.-D-ribo-hexofuranosyl)-2,4-(1H,3H)-pyrimidinedione 2.11 g of the product of the preceding stage is solubilized in the minimum amount of methylene chloride and 70 ml of a solution of methylene chloride and TFA (9/1) cooled down to 0° C. is added, followed by agitating for one hour and concentrating to dryness. After drying and chromatography on silica eluting with a methylene chloride/ethyl acetate mixture (6/4), 1.09 g of product is obtained.

By operating as previously for Examples 1 and 2, the 18 products represented in the following table were prepared which constitute Examples 3 to 20 of the present invention:

| $R_2$ | $R_4$ | $R_5$ | $R_6$ | $R_7$ | EX |
|---|---|---|---|---|---|
| OH | $CH_2NH_2$ | —$CH_2$—NH—C(=O)—$(CH_2)_{14}$—$CH_3$ | OH | H | 1 |
| F | —$CH_2NHCH_2CH_3$ | —$CH_2N_3$ | F | H | 2 |
| OH | $CH_2NH_2$ | $CH_2NH(CH_2)_6CH_3$ | OH | H | 3 |
| OH | $CH_2NH_2$ | —$CH_2$—N($CH_3$)—$(CH_2)_{11}CH_3$ | OH | H | 4 |
| OH | $CH_2NH_2$ | —$CH_2$—N($CH_3$)—$CH_2$—$C_6H_5$ | OH | H | 5 |
| OH | $CH_2NH_2$ | —$CH_2$—NH—CO—$C_6H_4$—$C_6H_5$ | OH | H | 6 |
| OH | $CH_2NH_2$ | —$CH_2$—NH—$C_6H_4$—$C_6H_{11}$ | OH | H | 7 |
| OH | $CH_2NH_2$ | $CH_2$—NH$(CH_2)_2$—$C_6H_4$—Cl | OH | H | 8 |

-continued

| R2 | R4 | R5 | R6 | R7 | EX |
|---|---|---|---|---|---|
| OH | CH$_2$NH$_2$ | CH$_2$—N(CH$_3$)—CH$_2$—(4-biphenyl) | S—(4-bromophenyl) | H | 9 |
| OH | CH$_2$NH$_2$ | CH$_2$—N(piperidinyl-4-phenyl) | Cl | H | 10 |
| OH | CH$_2$NH$_2$ | —CH$_2$—NH—(4-cyclohexylphenyl) | SCH$_2$—phenyl | H | 11 |
| OH | CH$_2$NH$_2$ | CH$_2$—N(piperidinyl-4-phenyl) | S—iPr | H | 12 |
| H | CH$_2$NH$_2$ | CH$_2$O(CH$_2$)$_2$CH$_3$ | F | H | 13 |
| OH | CH$_2$NH$_2$ | —CH$_2$—NH—C(=S)—NH—(4-bromophenyl) | OH | H | 14 |
| OH | CH$_2$NH$_2$ | CH$_2$—N(piperidine)—CH$_2$—phenyl | Cl | H | 15 |
| OH | CH$_2$NH$_2$ | CH$_2$—N(piperidine)—CH$_2$—phenyl | S—iPr | H | 16 |
| OH | CH$_2$NH$_2$ | —CH$_2$—NH—C(=O)—NH—(4-cyclohexylphenyl) | OH | H | 17 |
| OH | CH$_2$NH$_2$ | —CH$_2$—NH(CH$_2$)$_7$—CH$_3$ | OH | H | 18 |
| OH | CH$_2$NH$_2$ | —CH$_2$—NH(CH$_2$)$_9$—CH$_3$ | OH | H | 19 |
| OH | CH$_2$NH$_2$ | —CH$_2$—NH(CH$_2$)$_{13}$—CH$_3$ | OH | H | 20 |

EXAMPLE 21 OF PHARMACEUTICAL COMPOSITIONS

The compounds of formula (I) were prepared corresponding to the following composition:

| | |
|---|---|
| Product of Example 1 | 150 mg |
| Excipient s.q.f. | 1 g |

Detail of excipient starch, talc, magnesium stearate.
Pharmacological Study of the Products of the Invention
Method of Dilutions in a Liquid Medium A serie of tubes is prepared in which the same quantity of sterile nutritive medium is distributed. Increasing quantities of the product to be studied are distributed into each tube, then each tube is seeded with a bacterial strain. After incubation for twenty-four hours in a heating chamber at 37° C., the growth inhibition is evaluated by transillumination, which allows the minimal inhibitory concentrations (M.I.C.) to be determined, expressed in micrograms/cm$^3$.

The products of the invention, in particular the product of Example 1, show a good activity on the *S. aureus*, *S. pyogenes* and *E. faecium* strains.

What is claimed is:

1. A compound in all its possible isomeric forms as well as their mixtures of the formula

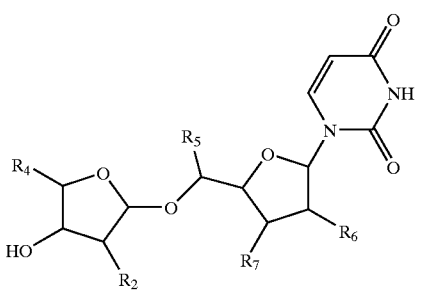

wherein R$_2$ is selected from the group consisting of hydrogen, halogen, alkyl, alkenyl or alkynyl of up to 12 carbon atoms, —OH, —O-alkyl, —OCO-alkyl up to 18 carbon atoms, —O-aryl or —OCO-aryl of up to 15 carbon atoms, R₄ is selected from the group consisting of —CH₂NH₂, —CH₂NHalkyl of up to 18 carbon atoms, —CH₂N(alkyl1)(alkyl2), alkyl1 and alkyl 2 are individually alkyl of up to 18 carbon atoms or R₄ is selected from the group consisting of unsubstituted or substituted —CH₂-guanidine, —CH₂-amidine, —CH₂-heterocycle, —CH₂—NH-heterocycle, —CH₂—NH-aryl or —CH₂—NH-heteroaryl, R₅ is selected from the group consisting of

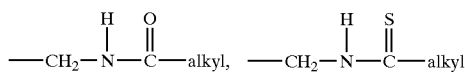

of up to 24 carbon atoms,

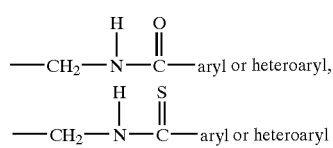

of up to 24 carbon atoms, —CH₂N₃,

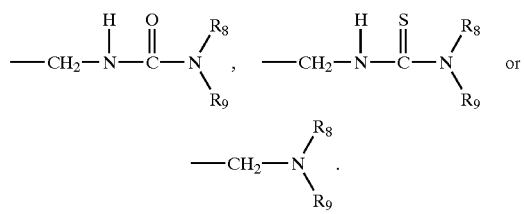

R₈ is hydrogen or alkyl of up to 4 carbon atoms,

R₉ is selected from the group consisting of unsubstituted or substituted alkyl of up to 18 carbon atoms, carbocyclic or heterocyclic having 5 or 6 ring members, aryl or heteroaryl, R₈ and R₉ also being able to form with the nitrogen atom which carries them a substituted or unsubstituted heterocycle, or R₅ is selected from the group consisting of unsubstituted or substituted —CH₂alkyl, —CH₂-aryl, —CH₂-heteroaryl, —CH₂Oalkyl, —CO₂alkyl, —CH₂S-alkyl of up to 16 carbon atoms, —CH₂S-aryl or —CH₂S-heteroaryl, R₆ is selected from the group consisting of hydrogen, halogen, —OH, —O-alkyl, —OCO-alkyl of up to 18 carbon atoms, —S-alkyl, —S-aryl or —S-heteroaryl of up to 12 carbon atoms, all the hereinable defined alkyl, aryl, heteroaryl, carbocyclic and heterocyclic when substituted are by at least one member of the group consisting of halogen, hydroxyl, alkyl and alkoxy of 1 to 4 carbon atoms, phenyl or phenylalkyl, the phenyl being unsubstituted or substituted by at least one member of the group consisting of halogen, phenyl or alkyl of 1 to 4 carbon atoms; and carbocyclic of 4 to 6 members; R₇ is hydrogen or a free, etherified or esterified OH, and its non-toxic, pharmaceutically acceptable acid addition salts.

2. A compound of claim 1 of the formula

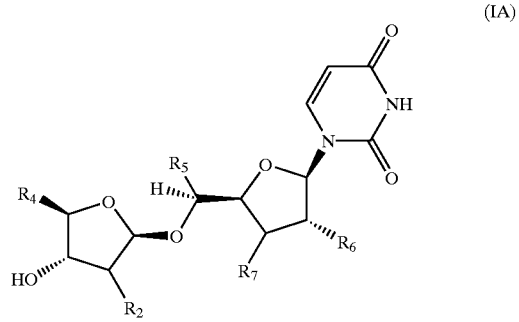

in which the various substituents retain the same meaning as in claim 1.

3. A compound of claim 1 wherein R₇ is hydrogen.
4. A compound of claim 1 wherein R₆ is —OH or fluorine.
5. A compound of claim 1 wherein R₂ is —OH.
6. A compound of claim 1 wherein R₂ is fluorine.
7. A compound of claim 1 wherein R₄ is —CH₂NH₂.
8. A compound of claim 1 wherein R₄ is —CH₂NHCH₃ or —CH₂NHC₂H₅.
9. A compound of claim 1 wherein R₅ is

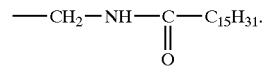

10. A compound of claim 1 wherein R₅ is

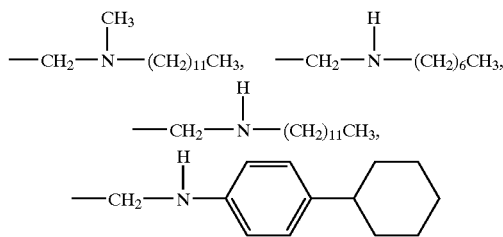

or —CH₂—NH-alkyl of 8 to 14 carbon atoms.

11. A compound of claim 1 which is
1-[5-O-(5-amino-5-deoxy-.beta.-D-ribofuranosyl)-3,6-dideoxy-6-[(1-oxohexadecyl)amino]-.beta.-D-ribohexofuranosyl]-2,4-(1H,3H)-pyrimidinedione.

12. An antibiotic composition comprising an antibiotically effective amount of a compound of claim 1 and a pharmaceutical carrier.

13. A process for the preparation of a compound of claim 1 comprising reacting a compound of the formula

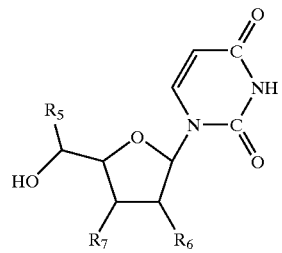

wherein the various substituents are as defined in claim 1 with a compound of the formula

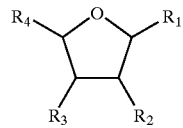
III wherein $R_1$ is halogen, —OC(NH)C(Hal)$_3$ wherein Hal is halogen, or

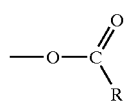

wherein R is alkyl of up to 18 carbon atoms, and $R_2$ and $R_4$ are defined as in claim 1, and $R_3$ is acetoxy or benzoyloxy to obtain the corresponding compound of formula (I) which is optionally subjected to one or more of the following operations: addition, saponification, substitution, condensation, reduction and salification to obtain the compound of formula I.

14. A compound of the formula

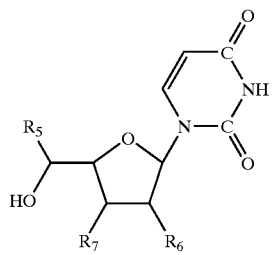
II wherein $R_5$, $R_6$ and $R_7$ are as defined in claim 1.

15. A method of combating bacterial infections in warm-blooded animals comprising administering to warm-blooded animals in need thereof an antibactericidally effective amount of a compound of claim 1.

16. The method of claim 15 wherein the compound is

1-[5-0-(5-amino-5-deoxy-.beta.-D-ribofuranosyl)-3,6-dideoxy-6-[(1-oxohexadecyl)amino]-.beta.-D-ribohexofuranosyl]-2,4-(1H,3H)-pyrimidinedione.

\* \* \* \* \*